United States Patent
Grams et al.

(10) Patent No.: US 6,242,455 B1
(45) Date of Patent: Jun. 5, 2001

(54) PYRIMIDIN-2,4,6-TRION DERIVATIVES, METHOD FOR PRODUCING THE SAME AND MEDICINAL PRODUCTS CONTAINING THESE COMPOUNDS

(75) Inventors: Frank Grams, Neuenburg-Zinken; Gerd Zimmermann, Linkenheim, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/445,460

(22) PCT Filed: Jun. 19, 1998

(86) PCT No.: PCT/EP98/03740

§ 371 Date: Mar. 22, 2000

§ 102(e) Date: Mar. 22, 2000

(87) PCT Pub. No.: WO98/58915

PCT Pub. Date: Dec. 30, 1998

(30) Foreign Application Priority Data

Jun. 23, 1997 (DE) ............................................. 197 26 427

(51) Int. Cl.[7] ...................... C07D 239/62; A61K 31/515; A61P 9/12
(52) U.S. Cl. ............................................. 514/270; 544/301
(58) Field of Search ............................. 514/270; 544/301

(56) References Cited

U.S. PATENT DOCUMENTS 5,616,497 * 4/1997 Strickland ............................ 435/262

FOREIGN PATENT DOCUMENTS

| 0 058 637 | 8/1982 | (EP) . |
| 0 640 594 | 3/1995 | (EP) . |
| 2 222 375 | 10/1974 | (FR) . |
| 96 17838 | 6/1996 | (WO) . |
| 97 23465 | 7/1997 | (WO) . |

OTHER PUBLICATIONS

Singh et al, Can. J. Chem., 42, 1964, 605–609.*
Ichiba et al, J. Org. Chem. 43, 1978, 469–472.*
Skinner et al, JACS, 1953, 75, 5909–5911.*
Stein et al, JACS, 1956, 78, 6185–6188.–*
Matjeka et al, J. Labelled Comp. Radiopharm., 23, 1986, pp. 969–980.*
Taylor et al, J. Org. Chem., 75, 1975, 2321–9.*
Peichl et al, Arch. Pharm. 317, 1984, 946–951.*
Wolff, Manfred E. editor, "Burger's Medicinal Chemistry, 4th ed.", John Wiley, New York, 1980, p. 178.*
Skinner et al., "Glycyl Derivatives of Aminobarbituric Acids", Journal of The American Chemical Society, vol. 75, 1953, pp. 5909–5911.
Singh et al., "Synthesis of 5–Acetamido Substituted Barbiturates", Canadian Journal of Chemistry, vol. 42, No. 3, 1964, pp. 605–609.
Stein et al., "Preparation of 1–Alkyluramil–7, 7–diacetic Acids", Journal of The American Chemical Society, vol. 78, 1956, pp. 6185–6188.
Falco et al., "Studies on condensed Pyrimidine Systems. IV. Some Thiazolo'5,4–d!pyrimidines", Journal of The American Chemical Society, vol. 72, 1950, pp. 3203–3205.
Matjeka et al., "Synthesis of stable isotope–enriched metabolites of theophylline", J. Labelled Comp. Radiopharm, vol. 23, No. 9, 1986, pp. 969–980.
Peichl et al., "Ylides of heterocycles, 6. Ylides of barbituric acieds with nicotinic acid derivatives as cationic moieties", Arch. Pharm. vol. 317, No. 11, 1984, pp. 946–951.
Ichiba et al., "Synthesis of fervenulin 4–oxide and its conversion to the antibiotics fervenulin and 2–methylfervenulone", J. Org. Chem., vol. 43, No. 3, 1978, pp. 469–472.
Talor et al., "Synthesis of the pyrimido '5,4–e!–as–triazine antibiotics fervenulin and 2–methylfervenulone", J. Org. Chem. (Joceah); 75; vol. 40 (16), pp 2321–9.
Chemical Abstracts, vol. 128, No. 18, May 4, 1998, 217352n.

* cited by examiner

Primary Examiner—John M. Ford
Assistant Examiner—Thomas A McKenzie
(74) Attorney, Agent, or Firm—Arent Fox Plotkin Kintner Kahn PLLC.

(57) ABSTRACT

Compounds of formula I

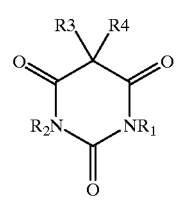

(I)

wherein R1, R2, R3 and R4 have the meanings indicated in the specification. The compounds are useful as inhibitors of metalloproteases of the M2, M3 family and the astacin subfamily of M12 and M13.

6 Claims, No Drawings

PYRIMIDIN-2,4,6-TRION DERIVATIVES, METHOD FOR PRODUCING THE SAME AND MEDICINAL PRODUCTS CONTAINING THESE COMPOUNDS

This application is a National Stage Entry of PCT/EP98/03740, which claims priority from German Application 19726427.1, filed Jun. 23, 1998.

The invention concerns new pyrimidine-2,4,6-trione derivatives, the production thereof and pharmaceutical preparations containing these. These compounds inhibit metalloproteases, in particular proteases from the M2 and M3 family, the astacin subfamily of M12 and M13. These protease families are defined in N. D. Rawlings and A. J. Barret, Methods Enzym. (1995) 248, 183–277.

BMP-1 is particularly preferred in the protease group M12 as an inhibition target of compounds of the invention. ECE and NEP from the M13 family are additionally preferred as well as ACE (peptidyl-dipeptidase A) from the subgroup M2.

Metalloproteases play a major role in many physiological and pathophysiological processes. Examples of this are the angiotensin converting enzyme (ACE) and neutral endopeptidase (NEP, EC 3.4.24.11) which are involved in the metabolism of a series of blood pressure-regulating peptides (e.g. angiotensin I and ANF (atrial natriuretic factor)). ACE catalyses the cleavage of angiotensin I to the hypertensive angiotensin II. NEP is responsible for the degradation of the vasodilating peptide ANF. Endothelin converting enzyme (ECE) cleaves the endogenous, inactive big-endothelin to the effective vasoconstrictor endothelin-1, a peptide composed of 21 amino acids. The inhibition of these enzymes is of major therapeutic significance for the treatment of high blood pressure, cardiac insufficiency, renal failure and stroke. BMP-1 (bone morphogenic factor 1) has been recognized to be a metalloprotease which plays a role in converting procollagen into fibrillary collagen. Inhibitors of this enzyme are suitable for the treatment of fibroses and sclerotic processes and can favourably influence scar formation in wound healing (Proc. Natl. Acad. Sci. USA 93, 5127 (1996); Science Vol., 271, 360 (1996)).

Whereas inhibitors of ACE have already been used therapeutically (e.g. captopril, enalapril, (Exp. Opinion Ther. Patents 6, 1147 (1996)), clinically usable active substances for metalloproteases such as NEP and ECE which are free of undesired side-effects and orally available are hitherto unknown. (Literature reviews: NEP: Pharmacol. Reviews 45, 87 (1993); ECE: Bioorg. Med. Chem. Lett. 6, 2317 (1996)) and references cited therein for inhibitors of the phosphoramidone type. There are still no known low-molecular inhibitors of BMP-1.

It has now been found that the claimed new pyrimidine-2,4,6-trione derivatives are very effective as metalloprotease inhibitors with a good oral availability.

Thus the present invention concerns substances of the general formula I,

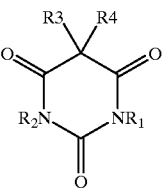

in which

R1 and R2 can be independently of one another H, alkenyl or alkyl

R3 represents a group W-V in which W represents a bond or a linear or branched alkyl or alkenyl group which can optionally be interrupted by oxygen, sulphur or nitrogen, which can be substituted by hydroxy, amino, mercapto, alkoxy, oxo, carboxy, acyl, alkyl, aralkyl, aryl or heteroaryl groups and V can represent H, a monocyclic or bicyclic, saturated or unsaturated ring which can optionally contain 1 to 4 nitrogen, oxygen or sulphur atoms and can optionally be substituted by a hydroxy, amino, mercapto, alkoxy, oxo, carboxy, acyl, acylamido, alkyl, aralkyl, aryl or heteroaryl groups.

R4 can be a residue —N(R13)—C(O)—R5, —N(R13)—C(O)—OR5, —N(R13)—SO2—R5, —N(R13)—C(S)—R5, —N(R13)—C(S)—OR5, —N(R13)—C(O)—CR14R15(—CR15R17)$_n$—C(O)—R5, or —N(R13)—CR14R15(—CR16R17)$_n$—C(O)—R18 each of which is bound to the central pyrimidine ring via the nitrogen atom n equals 0 or 1

R13 has the meaning mentioned above for R3 or optionally forms a 4- or 7-membered heterocycle with R14 or R16 and R5 represents an alkyl, cycloalkyl, aralkyl, aryl or heteroaryl residue wherein these residues can be substituted by hydroxy or amino groups or halogen. R14, R15, R16 and R17 independently of another denote hydrogen, a Cα residue of a proteinogenic amino acid, alkyl, cycloalkyl, aryl, heteroaryl, aralkyl or heteroaralkyl; R14 and R15 or alternatively R16 and R17 can together form a 3- or 7-membered carbocycle R18 denotes OH or N(R6R7), wherein R6 equals H or can be alkyl, cycloalkyl, aralkyl, aryl or heteroaryl and R7 represents a group which together with the N-atom represents a proteinogenic or non-proteinogenic α or β amino acid or amino acid amide and additionally R6 and R7 together can form a 4- to 7-membered ring which optionally contains heteroatoms such as oxygen, sulphur or nitrogen, and optionally can be substituted by alkyl, aralkyl, aryl or heteroaryl.

Additionally pharmacologically tolerated salts and esters of the general structure I as well as the use of these compounds to produce pharmaceutical preparations.

R1 and R2 independently of one another are preferably H or methyl, particularly preferably H R3 preferably represents H, alkyl, cycloalkyl or aryl, heteroaryl, aralkyl or heteroaralkyl. H or $C_1$–$C_6$ alkyl is especially preferred.

R4 is preferably a residue of a proteinogenic or non-proteinogenic α or β amino acid which is linked to the central pyrimidine ring via the nitrogen atom and whose carboxyl group is either free or linked to Rx or is a group —NH—CO—CHR14—CO—Rx wherein Rx represents hydroxy, alkoxy or the group —N(R6, R7) described above.

R13 is preferably H or alkyl.

R14 and R16 are independently of one another preferably alkyl or cycloalkyl or the Cα residue of a proteinogenic amino acid.

R15 and R17 are preferably hydrogen.

n is preferably 0.

A combination of the preferred compounds mentioned above is quite especially preferred.

Alkyl should in all cases be a straight-chained or branched $C_1$–$C_{10}$ preferably $C_1$–$C_6$ alkyl chain such as e.g. methyl, ethyl, propyl, isopropyl, butyl, isobutyl, pentyl or hexyl. An alkenyl group denotes unsaturated residues with 3–6 C atoms such as e.g. allyl, but-2-enyl, hexa-2,4-dienyl. Cycloalkyl represents a 3–7-membered ring in which a CH2 group can be substituted by O or NH such as among others a cyclopropyl, cyclobutyl, cyclopentyl, cyclohexyl or a cycloheptyl ring, preferably a cyclopenzyl or cyclohexyl ring.

Alkoxy groups denote a combination of an alkyl group according to the above definition with an oxygen atom e.g. methoxy, ethoxy, propoxy, isopropoxy, butoxy and pentoxy groups, of which methoxy, ethoxy, isopropoxy and butoxy are preferred.

Aryl groups denote an aromatic carbon residue preferably one with 6–10 C atoms in particular a phenyl or naphthyl group which can in each case be linked to hydroxy or amino which can optionally be substituted by alkyl groups, or to alkyl or alkoxy groups. Heteroaryl groups are aromatic residues that are composed of unsaturated carbon atoms and heteroatoms such as nitrogen, oxygen and sulphur, wherein the sum of the ring atoms can be between 5 and 10. Examples of this are an imidazole, thiazole, triazole, pyridyl, pyrimidyl, pyrazinyl, indolyl and purinyl residue. An imidazolyl, thiazolyl, pyridyl or indolyl residue are preferred. Aralkyl groups denote residues in which one of the previously defined alkyl groups is linked to one of the previously characterized aryl residues, the benzyl residue being preferred in this case. A heteroaralkyl residue represents a combination of one of the alkyl groups defined above with one of the aryl residues described above. A pyridylmethyl, imidazolylmethyl and thiazolylmethyl residue are preferred. If not stated otherwise cycloalkyl, aryl and heteroaryl residues are substituted once to three-times independently of one another by alkyl, hydroxy, alkoxy, amino, alkylamino, dialkylamino, mercapto or thioalkyl.

Acyl residues are straight-chained or branched $C_2$–$C_{10}$ carbonylalkyls, $C_2$–$C_6$ acyl residues are preferred.

If R6 and R7 together with the nitrogen atom to which they are bound form a ring, then this is a 5-membered to 7-membered ring, preferably a six-membered ring. A piperidine, piperazine, tetrahydroquinoline and tetrahydroisoquinoline, bicyclo(9.4.0)pentadecyl and 1.2.3.4-tetrahydrobenzo(g)isoquinoline ring are particularly preferred.

If R14 and R15 or R16 and R17 form a carbocycle then a 4-, 5- or 6-membered ring is preferred.

The monocycle stated under V is understood as saturated or unsaturated ring systems with 3–8, preferably 5–7 carbon atoms which can optionally be interrupted once or several times by heteroatoms such as nitrogen, oxygen or sulphur, in particular a cyclopentyl, cyclohexyl, cycloheptyl, morpholinyl, thiamorpholinyl, piperidinyl, piperazinyl, tetrahydrofuranyl, tetrahydropyranyl, phenyl, pyridyl, pyrimidinyl, pyridazinyl, pyrazinyl, furyl, thiophenyl, imidazolyl, thiazolyl, oxazolyl, isothiazolyl, isoxazolyl, 1,2,3-triazolyl or 1,2,4-triazolyl residue. Lower alkyl, alkoxy and halogen come especially into consideration as substituents. The bicycle stated under V is preferably residues such as a naphthyl, tetrahydronapthyl, decalinyl, quinolinyl, isoquinolinyl, tetrahydroquinolinyl, tetrahydroisoquinolinyl, indolyl, benzimidazolyl, indazolyl, oxindolyl, benzofuranyl, benzothiophenyl, benzthiazolyl, benzoxazolyl or purinyl residue but in particular a naphthyl, quinolinyl, isoquinolinyl, tetrahydroquinolinyl, indolyl or benzimidazolyl residue.

Several examples for non-proteinogenic amino acids are listed in the following:

2-amino-2-methylbutanecarboxylic acid, 2-fluoro-β-alanine, β-alanine, 2,3-diaminosuccinic acid, β-aminoisobutyric-carboxylic acid, isoserine, 2-amino-3-hydroxy-4-methylpentanecarboxylic acid, 2-amino-3-methoxy-butanecarboxylic acid, diaminopropionic acid, 2-amino-2-methyl-3-hydroxypropanecarboxylic acid, 2-amino-2-methylbutanedicarboxylic acid, 2-amino-3-hydroxy-3-methylbutanecarboxylic acid, 2,3-diamino-propionic acid, 2-amino-2-methyl-3-hydroxypropanecarboxylic acid, 2-amino-2-methylbutanedicarboxylic acid, 2-amino-2-methyl-4-pentene carboxylic acid, 2-amino-3-methoxypropanecarboxylic acid, l-amino-l-cyclo-hexane-carboxylic acid, 1-amino-l-cyclopentanecarboxylic acid, 1-aminocyclobutanecarboxylic acid, 1-aminocyclopropane-carboxylic acid, 2-(2-furyl)-glycine, 2-amino-3-fluorobutyric acid, 2-aminoisobutyric acid, 3-chloro-alanine, 3-fluoronorleucine, 3-fluoro-valine, 3-fluoroalanine, 3-methoxyvaline, α-cyano-alanine, α-methyl-leucine, β-chloroalanine, β-cyano-alanine, β-hydroxy-leucine, β-hydroxyaspartic acid, 3-hydroxy-aspartic acid, 2-aminobutyric acid, allylglycine, γ-methylleucine, homoserine, norleucine, norvaline, tert.-leucine, 2,3-diaminosuccinic acid, 2-amino-4-pentene-carboxylic acid, 2-aminoheptanecarboxylic acid, 2-cyclopropyl-2-methylglycine, 4-thiaisoleucine, allothreonine, α-methylaspartic acid, α-methylserine, β-hydroxynorvaline, β-methylaspartic acid, homocysteine, O-methylserine, penicillamine, propargylglycine, vinylglycine, H-4,5-dehydro-Leu-OH, H-α-Me-Val-OH, H-propargyl-Gly-OH, H-allo-Ile-OH, H-Pra-OH, H-trans-4,5-dehydro-Lys-OH, 3-hydroxyaspartic acid, 6-hydroxy-norleucine, alloisoleucine, allyl glycine, α-amino-N-butyric acid, γ-methylleucine, α,β-diaminosuccinic acid, O-carbamoylserine, S-methyl-cysteine, citrulline, cyclohexylalanine, α,γ-diaminobutyric acid, α,γ-diaminopropionic acid, methionine sulfoxide, Ca-methylalanine, N-methylglycine (sarcosine), napthylalanine, ornithine, 1,2,3,4-tetrahydroisoquinoline-3-carboxylic acid, homocysteine, 4-hydroxy-proline, 5-hydroxy-lysine, aminobutyric acid, pantonine, glucosaminic acid, lanthionine, aliine, dopa, kanavanin, oletopin, β-lysine, β-alanine. D-amino acids can also be used as well as L-amino acids.

If compounds of the general formula I contain one or several asymmetric carbon atoms, optically active compounds of the general formula I are also a subject matter of the present invention.

Compounds of the general formula I can be prepared by well-known methods preferably in which a) compounds of the general formula II

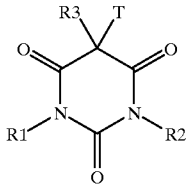
(II)

in which R1, R2 and R3 have the above-mentioned meanings and T represents a leaving group such as Hal or OSO2R8, wherein Hal denotes chlorine, bromine or iodine and R8 denotes an aryl or a methyl residue are reacted with a compound-of the general formula III

(III)

in which R6 and R7 have the above-mentioned meanings whereby functional groups can be protected by common protecting groups and optionally converted into pharmacologically tolerated salts, or b) compounds of the general formula IV

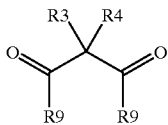
(IV)

in which R3 has the above-mentioned meanings, R9 represents alkoxy and R4 has the meaning given above are reacted with a compound of the general formula V

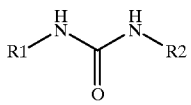
(V)

in which R1 and R2 have the above-mentioned meanings and optionally converted into pharmacologically tolerated salts or c) in the case that R4 is bound to the central pyrimidine ring via a carboxamido, carbamoyl, thiocarbamoyl, ureido, sulfonamido residue or an amino residue, a compound of the general formula VI

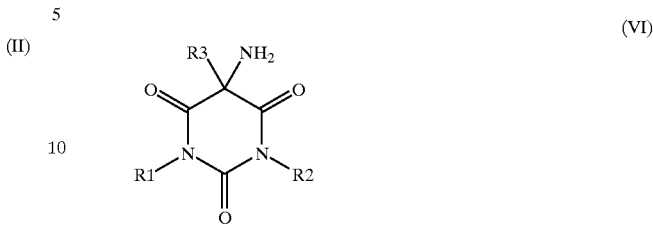
(VI)

in which R1, R2 and R3 have the above-mentioned meanings is reacted with a compound of the general formula VII or VIII

R11-D-Hal (VII)
R11-N-A (VIII)

in which R11 represents an optionally substituted alkyl, cycloalkyl, aryl or heteroaryl residue, D=C(O), O—C(O), SO2 or a valency dash, halogen=chlorine, bromine or iodine and A represents oxygen or sulphur, and optionally converted into pharmacologically tolerated salts.

Compounds of the general formula II are known in the literature. Thus 2,4,6-pyrimidine-triones brominated at the 5-position can be prepared by reacting appropriate bromomalonic acid dialkyl esters with urea (e.g. Acta Chim. Acad. Sci. Hung. 107 (2), 139 (1981)). The corresponding brominated or chlorinated compounds of the general formula II are obtained by reacting 2,4,6-pyrimidine-triones substituted by R3 at the 5-position with bromine (analogously to J. pr. Chemie 136, 329 (1993) or J. Chem. Soc. 1931, 1870) or sulfuryl chloride (J. Chem. Soc. 1938, 1622).

Amines of the general formula III are commercially available or are usually known in the literature.

Compounds of the general formula IV are reacted according to known methods with ureas (formula V) (see e.g. J. Med. Chem. 10, 1078 (1967) or Helvetica Chim. Acta 34, 459 (1959) or Pharmacie 38 (1), 65 (1983)).

The reactions are usually carried out in an alcohol such as methanol, ethanol or butanol in the presence of the corresponding sodium alcoholate at temperatures between 40° C. and 100° C.

Compounds of the general formula IV are known in the literature or can be prepared according to methods known from the literature. They can be prepared for example by weak acid hydrolysis of the corresponding bislactim ethers (see J. Chem. Soc. Chem. Comm. 5, 400 (1990)). Other methods of preparation are for example described in Farmaco Ed. Sci. 31 (7), 478 (1976) and Aust. J. Chem., 23 (6), 1229 (1970).

Compounds of the general formula VI can easily be prepared by reacting an appropriately substituted acetamidomalonic ester according to method b) and subsequent hydrolytic cleavage of the acetyl group (see Can. J. Chem. 42 (3), 605 (1964)).

Acyl chlorides of the general formula VII are known or can be prepared according to well-known methods from the corresponding carboxylic acids. The reaction is usually carried out using thionyl chloride or phosphorus tribromide or phosphorus pentabromide or phosphorus trichloride or pentachloride in inert solvents such as dichloromethane, diethyl ether, dioxane or tetra-hydrofuran at temperatures of 0° C. to 50° C. preferably between 20° C. and 40° C.

Chloroformic acid esters of the general formula VII are known in the literature or can be obtained according to generally known methods from the corresponding alcohols by reaction with phosgene or diphosgene. The reaction proceeds in inert solvents such as e.g. diethyl ether, dichloromethane, dioxane, tetrahydrofuran or toluene at temperatures between −20° C. and 20° C. In the case of phosgene the reaction is carried out in the presence of bases usually tertiary amines such as e.g. triethylamine or pyridine.

Sulfonic acid chlorides of the general formula VII are known or can be prepared analogously to the methods described from the corresponding sulfonic acids by reaction with phosphorus pentachloride or thionyl chloride. The reaction is usually carried out in inert solvents such as e.g. dimethylformamide or also without a solvent at temperatures of 20° C. to 180° C., preferably at 50° C. to 100° C.

Isocyanates of the general formula VIII are known or can be prepared according to methods known in the literature. Thus for example corresponding alkyl-halogenides of the general formula R11-Hal can be reacted with potassium cyanate analogously to Synthesis 1978, 760. Further methods are the reactions of an acid amide of the general formula R11-CONH2 with oxalyl chloride, the thermal decomposition of an acid azide of the general formula R11-CON3 or the reactions of an amine of the general formula R11-NH2 with phosgene (analogously to Ann. Chem. 562, 110).

Carboxylic acid halogenides, sulfonic acid halogenides or chloroformic acid esters of the general formula VII are usually reacted with amines of the general formula VI in a solvent such as dichloromethane, dimethylformamide or pyridine with addition of an auxiliary base such as triethylamine or 4-dimethylaminopyridine at a temperature between −10° C. and 50° C., preferably at room temperature.

Compounds of the general formula I can contain one or several chiral centres and can then be present in a racemic or optically active form. The racemates can be resolved into the enantiomers according to known methods. Diastereomeric salts, which can be separated by crystallization, are preferably formed from the racemic mixtures by reaction with an optically active acid such as e.g. D-tartaric or L-tartaric acid, mandelic acid, malic acid, lactic acid or camphorsulfonic acid or with an optically active amine such as e.g. D-phenylethylamine, or L-phenylethylamine, ephedrine, quinidine or cinchonidine.

Alkali salts, ammonium salts, acetates or hydrochlorides are used as pharmacologically tolerated salts which are prepared in the usual manner for example by titrating the compounds with inorganic or organic bases or inorganic acids such as e.g. sodium hydroxide, potassium hydroxide, aqueous ammonia, amines such as e.g. triethylamine or hydrochloric acid. The salts are usually purified by precipitation from water/acetone.

The new substances of formula I according to the invention and salts thereof can be administered enterally or parenterally in a liquid or solid form. In this connection all common forms of administration come into consideration such as tablets, capsules, dragees, syrups, solutions, suspensions etc. Water is preferably used as an injection medium which contains the usual additives such as stabilizers, solubilizers and buffer.

Such additives are e.g. tartrate buffer and citrate buffer, ethanol, complexing agents (such as ethylene diaminetetraacetic acid and non-toxic salts thereof), high molecular polymers (such as liquid polyethylene oxide) to regulate viscosity. Liquid carriers for injection solutions have to be sterile and are preferably dispensed into ampoules. Solid carriers are e.g. starch, lactose, mannitol, methylcellulose, talcum, highly-dispersed silicic acids, higher molecular fatty acids (such as stearic acid), gelatin, agar-agar, calcium phosphate, magnesium stearate, animal and vegetable fats, solid high molecular polymers (such as polyethylene glycols); suitable preparations for oral administration can optionally contains flavourings and sweeteners.

The dosage can depend on various factors such as mode of application, species, age and/or individual state. The daily dose to be administered is about 10-1000 mg/person, preferably 100–500 mg/person and can be administered once or divided into several applications.

In addition to the compounds listed in the examples and compounds derived by combining all meanings of the substituents stated in the claims, the following barbituric acid derivatives which can be prepared according to the above-mentioned methods are preferred within the sense of the present invention:

1. N-(5-benzyl-2,4,6-trioxo-hexahydro-pyrimidin-5-yl)-malonic acid
2. N-(5-benzyl-2,4,6-trioxo-hexahydro-pyrimidin-5-yl)-malonic acid methyl ester
2. N-(5-benzyl-2,4,6-trioxo-hexahydro-pyrimidin-5-yl)-N'-methyl-malonamide
4. 3-(2,4,6-trioxo-hexahydro-pyrimidin-5-ylamino)-propionic acid
5. 3-(1H-indol-3-yl)-2-(2,4,6-trioxo-hexahydro-pyrimidin-5-ylamino)-propionic acid
6. 3-(4-hydroxy-phenyl)-2-{[1-2,4,6-trioxo-hexahydro-pyrimidin-5-ylamino)-cyclobutanecarbonyl]-amino}-propionic acid
7. 1-(2,4,6-trioxo-hexahydro-pyrimidin-5-yl)-pyrrolidine-2-carboxylic acid

EXAMPLE 1

N-(2,4,6-Trioxo-5-phenyl-hexahydro-pyrimidin-5-yl)-malonamic acid methyl ester 2 g 5-amino-5-phenyl-2,4,6-trioxopyrimidine is dissolved in 20 ml acetonitrile and admixed with 1.5 ml N-methyl-morpholine. 1.03 ml malonic acid monomethyl ester chloride is added dropwise while stirring and cooling on ice and the suspension is stirred for 2 hours at room temperature. The precipitate is suction filtered, washed with acetonitrile, water and again with acetonitrile and dried. 1.97 g (68%) of the title compound is obtained.

TLC $R_f$=0.1 (silica gel, isohexane, acetone, glacial acetic acid 7:3:0.1)

MS 319 m/e

EXAMPLE 2

N-methyl-N'-(2,4,6-trioxo-5-phenyl-hexahydro-pyrimidin-5-yl)-malonamide 160 mg of the compound obtained in example 1 is admixed with 7 ml saturated methanolic methylamine solution. Crystallization starts after a short time. The suspension is evaporated after 2 hours and the residue is triturated with ether, suction filtered and dried. 149 mg (93%) of the title compound is obtained.

TLC $R_f$=0.3 (silica gel, methylene chloride/methanol 9:1)

MS 318 m/e

EXAMPLE 3

3,3-Dimethyl-2-(2,4,6-trioxo-5-phenyl-hexahydro-pyrimidin-5-ylcarbamoyl)-butyric acid ethyl ester If the malonic acid monomethyl ester chloride in example 1 is substituted by t-butylmalonic acid-monoethyl ester chloride, then the title compound is obtained in a yield of 94%.

TLC $R_f$=0.62 (silica gel, methylene chloride/methanol 9:1)

MS 389 m/e

EXAMPLE 4

3.3-Dimethyl-2-(2,4,6-trioxo-5-phenyl-hexahydro-pyrimidin-5-ylcarbamoyl)-butyric acid 1 g of the product obtained in example 3 is dissolved in ethanol and admixed with 0.5 g potassium hydroxide in 1 ml water. After 2 days at room temperature the reaction mixture is evaporated, the residue is admixed with ice water and ethyl acetate and acidified to pH 3 with 2N HCl. The ethyl acetate phase is dried and evaporated. 0.7 g (75%) of the title compound is obtained.

TLC $R_f$=0.5 (silica gel, methylene chloride/methanol/water 9:1:1)

MS 361 m/e

EXAMPLE 5

ACE-fluorescence assay for the determination of the $IC_{50}$ value

Literature: Amos Carmel and Arieh Yaron, Eur. J. Biochem. 787, 265–273 (1978). An Intramolecularly Quenched Fluorescent Tripeptide as a Fluorogenic Substrate of Angiotensin-I-Converting Enzyme and of Bacterial Dipeptidyl Carboxypeptidase.

Enzyme: Angiotensin-converting enzyme from rabbit lung (EC.3.4.15.1), Fluka (3.3 U/µg)

Substrate: Abz-Gly-Phe(NO2)-Pro, M-1100 Bachem $C_{23}H_{29}N_5O_7$, MW=483.4

Assay buffer: 0.05 Tris-HCl
　0.1M NaCl
　pH 8.0

Excitation: 360 nm (excitation slit: 8 nm)

Emission: 410 nm (emission slit: 10 nm)

Temperature: 36° C.

Substrate stock solution: 0.4 nM in assay buffer

Enzyme stock solution: 50 µl/ml assay buffer

Inhibitor stock solution: 1 mM in DMSO diluted in assay buffer

Measuring cuvette: 50 µl substrate (yields 20 µM)
　100 µl enzyme
　0 to 100 µl inhibitor stock solution
　(0 to 100 µM)
　fill up remainder to 1 ml Substrate, inhibitor and buffer are added together in a heated measuring cuvette and the enzyme reaction is started by addition of enzyme. The increase in fluorescence over time (200 s) is monitored in a time scan. The respective initial rate is determined from the increase.

The $IC_{50}$ value can be determined as follows:

$$V=V_0/(1+[I]/IC_{50})$$

V=initial rate $V_0$=initial rate without inhibitor

[I]=inhibitor concentration

TABLE 1

| Pharmacological data: | |
|---|---|
| Compound | $IC_{50}$ |
| example 4 | 159 µM |

What is claimed is:

1. A compound of formula I

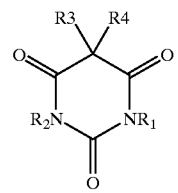

(I)

wherein $R_1$ and $R_2$ are hydrogen, $R_3$ is selected from the group consisting of hydrogen, phenyl and benzyl and $R_4$ is a group —NH—CO—CHR$_{13}$—CO—R$_x$, wherein $R_x$ is selected from the group consisting of hydroxyl, $C_1$–$C_6$ alkoxy and —N(R$_6$R$_7$), $R_{13}$ is hydrogen or $C_1$–$C_6$ alkyl, $R_6$ is hydrogen and $R_7$ is methyl or hydrogen, or a pharmacologically tolerated salt thereof.

2. The compound of claim 1, wherein the compound is selected from the group consisting of N-(2,4,6-trioxo-5-phenyl-hexahydro-pyrimidin-5-yl)-malonamide acid methyl ester, N-methyl-N'-(2,4,6-trioxo-5-phenyl-hexahydro-pyrimidin-5-yl)-malonamide, 3,3-dimethyl-2-(2,4,6-trioxo-5-phenyl-hexahydro-pyrimidin-5-ylcarbamoyl)-butyric acid ethyl ester, 3,3-dimethyl-2-(2,4,6-trioxo-5-phenyl-hexahydro-pyrimidin-5-ylcarbamoyl)-butyric acid, N-(5-benzyl-2,4,6-trioxo-hexahydro-pyrimidin-5-yl)-malonic acid, N-(5-benzyl-2,4,6-trioxo-hexahydro-pyrimidin-5-yl)-malonic acid methyl ester, N-(5-benzyl-2,4,6-trioxo-hexahydro-pyrimidin-5-yl)-N'-methylmalonamide and 3-(2,4,6-trioxo-hexahydro-pyrimidin-5-ylamino)-propionic acid.

3. A pharmaceutical composition comprising a compound according to claim 1, together with a pharmaceutically acceptable carrier.

4. A pharmaceutical composition comprising a compound according to claim 2, together with a pharmaceutically acceptable carrier.

5. A method of inhibiting a matrix metalloprotease associated disease in a patient in need of such inhibition, wherein the disease is selected from high blood pressure, cardiac insufficiency, renal failure, stroke, fibroses, sclerotic processes, and scar formation in wound healing comprising administration to the patient a matrix metalloprotease inhibiting-effective amount of a compound according to claim 1.

6. A method of inhibiting a matrix metalloprotease associated disease in a patient in need of such inhibition, wherein the disease is selected from high blood pressure, cardiac insufficiency, renal failure, stroke, fibroses, sclerotic processes, and scar formation in wound healing comprising administration to the patient a matrix metalloprotease inhibiting-effective amount of a compound according to claim 2.

* * * * *